United States Patent [19]

Harris et al.

[11] 4,051,236

[45] Sept. 27, 1977

[54] INHIBITION OF BLOOD PLATELET AGGREGATION

[75] Inventors: Don Navarro Harris, Somerset; Marie B. Phillips, Skillman; Harold Jacob Goldenberg, Highland Park, all of N.J.

[73] Assignee: E. R. Squibb & Sons, Inc., Princeton, N.J.

[21] Appl. No.: 688,501

[22] Filed: May 20, 1976

Related U.S. Application Data

[63] Continuation-in-part of Ser. No. 332,847, Feb. 15, 1973, abandoned.

[51] Int. Cl.² .............................................. A61K 35/14
[52] U.S. Cl. .................................... 424/101; 195/1.8; 424/256; 424/318
[58] Field of Search ......................... 424/256, 101, 318

[56] References Cited

U.S. PATENT DOCUMENTS

| 3,755,565 | 8/1973 | Spraggins | 424/101 |
| 3,974,195 | 8/1976 | Youngdale | 424/318 |

Primary Examiner—Ethel G. Love
Attorney, Agent, or Firm—Lawrence S. Levinson; Merle J. Smith; Burton Rodney

[57] ABSTRACT

The activity of $PGE_1$ in inhibiting aggregation of blood platelets is enhanced by employing $PGE_1$ in combination with certain inhibitors of cyclic 3',5'-adenosine monophosphate phosphodiesterase (PDE).

7 Claims, No Drawings

INHIBITION OF BLOOD PLATELET AGGREGATION

REFERENCE TO OTHER APPLICATIONS

This application is a continuation-in-part of application Ser. No. 332,847, filed Feb. 15, 1973, now abandoned.

OBJECTS OF THE INVENTION

It is an object of the present invention to provide compounds which potentiate the effect of $PGE_1$ in inhibiting the aggregation of blood platelets on storage. Another object is to provide blood platelet compositions having reduced tendency to aggregate. A further object is to provide a method for inhibiting the tendency of blood platelets to aggregate. These and other objects of the present invention will be apparent from the following description.

SUMMARY OF THE INVENTION

It has now been found that the effectiveness of prostaglandin $E_1$ ($PGE_1$) in inhibiting the aggregation of blood platelets is potentiated by employing the $PGE_1$ in combination with inhibitors of PDE.

BACKGROUND OF THE INVENTION

During the high-speed centrifugation of plateletrich plasma, massive aggregates are formed. Prostaglandin $E_1$ ($PGE_1$) is one of the most potent inhibitors of platelet aggregation known. The use of $PGE_1$ in improving the preparation of human platelet concentrates from plasma rich in platelets and from whole blood is described by Shio et al., Science, 175: 536, 1972. Shio et al. found that the addition of $PGE_1$ at a concentration of $10^{-8}$ to $10^{-7}$ molar prevented the clumping (aggregation) of platelets in whole blood, platelet rich plasma and platelet concentrates.

The use of $PGE_1$ in preventing clumping of platelets in stored whole blood and platelet concentrates either at room temperature or in the cold and with a variety of anticoagulants is described by Becker et al., Science, 175: 538, 1972.

The addition of $PGE_1$ at a concentration of $2.2 \times 10^{-8}$M to whole blood does not impair the effectiveness of fresh platelet concentrates and significantly improves platelet recovery in vitro according to Valeri et al., Science, 175: 539, 1972.

DETAILED DESCRIPTION

The present invention is directed to compounds which potentiate the effectiveness of prostaglandin $E_1$ ($PGE_1$) in inhibiting the aggregation of blood platelets. The compounds of the present invention which potentiate the effectiveness of $PGE_1$ have in common the fact that they are inhibitors of cyclic AMP phosphodiesterase of human blood platelets.

The inhibition of blood platelet aggregation according to the present invention is obtained by contacting blood platelets with a concentration of from about $10^{-6}$ molar to about $10^{-9}$ molar $PGE_1$ in combination with from about 0.1 mM to about 4mM of one of the following compounds:

1. 2-[(Dimethylamino)methyl]-3,4-dihydro-7-methoxy-1(2H)-naphthaleneone or its hydrochloride (1:1)

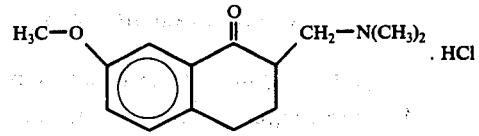

2. 4-(Butylamino)-1-ethyl-1H-pyrazolo[3,4-b]pyridine-5-carboxylic acid, ethyl ester

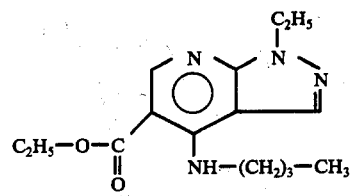

3. Hexamethylenebis(trimethylammonium-2-anthraquinonesulfonate)

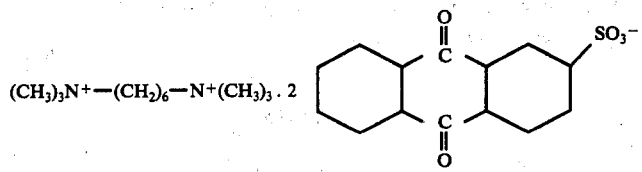

4. 6,7-Diethoxy-1-(4,5-diethoxybenzyl)isoquinoline or its hydrochloride

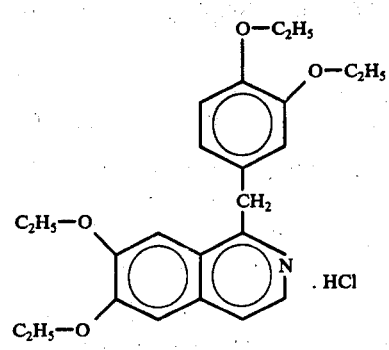

5. 4-Chloro-1-ethyl-3-methyl-1H-pyrazolo[3,4-b]pyridine-5-acetonitrile

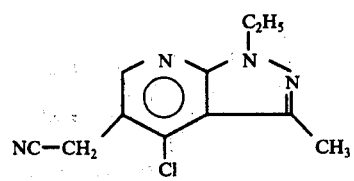

6. 1-Ethyl-4-(isopropylidenehydrazino)-3-methyl-1H-pyrazolo[3,4-b]pyridine-5-carboxylic acid, ethyl ester, or its hydrochloride, hemihydrate

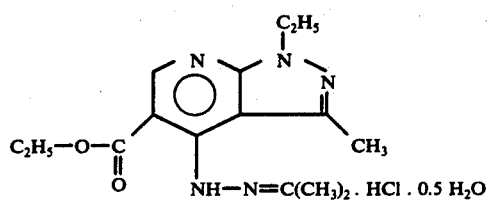

7. 2-Methyl-6-phenyl-4-(1-piperidinyl)-2H-pyrazolo[3,4-b]-pyridine or its hydrochloride (1:2)

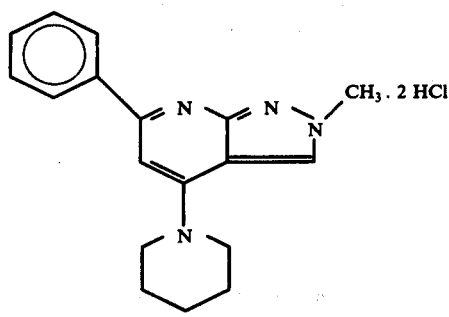

8. 3-Ethyl-7,12-dimethylpyrazolo[4',3':5,6]pyrido[4,3-b]-[1,5]benzodiazepin-6(3H)-one

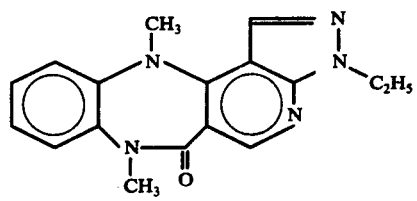

9. 3-Ethyl-7,12-dihydro-9-methoxy-7,12-dimethyl-pyrazolo[3',4':2,3]pyrido[4,5-b][1,5]benzodiazepin-6(3H)-one

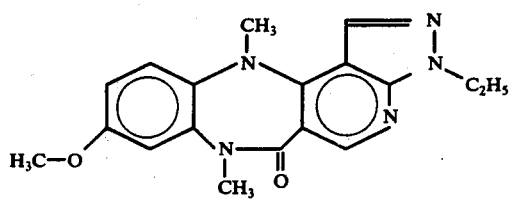

10. 4-(Butylamino)-1H-pyrazolo[3,4-b]pyridine-6-carboxylic acid, ethyl ester

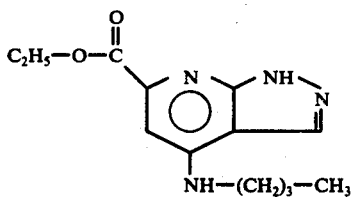

11. 4-(Butylamino)-1-ethyl-1,7-dihydro-7-hydroxy-5H-furo[3,4-e]pyrazolo[3,4-b]pyridin-5-one

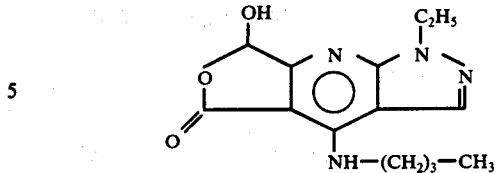

12. 10-Chloro-3-ethyl-7,12-dimethyl-7,12-dihydro-pyrazolo[4',3':5,6]pyrido[4,3-b][1,5]benzodia-zepin-6(3H)-one

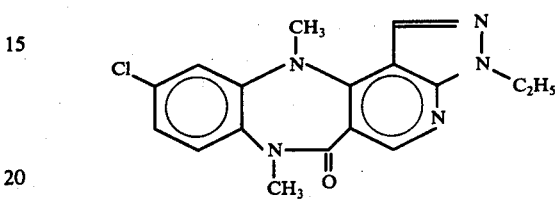

The following method is used to determine activity of the compounds of the present invention:

A. Preparation of Phosphodiesterase. Cyclic 3',5' adenosine monophosphate phosphodiesterase (PDE) is prepared from human platelet concentrates, by the procedure of Mills and Smith, Biochem. J. 121, 185 (1971). After the removal of small amounts of contaminating leukocytes and erythrocytes, the platelets are suspended in 0.154 M saline and sonicated using a Branson Sonifier. The disrupted platelets are centrifuged at 17,500g, and the supernatant dialyzed overnight at 0°–4° C against Tris-HCl buffer, pH 7.5. This supernatant enzyme preparation is divided into samll aliquots and stored at −70° C until used.

B. Phosphodiesterase Assay. Phosphodiesterase activity is assayed at low substrate concentration (0.06 μM) using the radiometric procedure developed by Brooker et al., Biochemistry, N.Y. 7, 4177 (1968). This assay is based on the conversion of $^3$H-cyclic 3',5'-adenosine monophosphate ($^3$H-cyclic AMP) by PDE to $^3$H-5'-adenosine monophosphate ($^3$H-5'-AMP), which is further hydrolyzed to $^3$H-adenosine by the nucleotidase of cobra venom. The reaction is stopped by the addition of an anion-exchange resin which binds and quenches all charged nucleotides and leaves $^3$H-adenosine as the only labelled compound to be counted. All assays are performed between 20 and 30% of the total enzymatic reaction, where the reaction rate is a linear function of enzyme protein concentration and time.

C. Aggregation of Blood Platelets. Platelet aggregation is studied photometrically using a Born MKIII aggregometer as described by Born, Nature, Lond., 194 (1962). Platelet rich plasma (PRP) is prepared by centrifuging freshly drawn human blood 200 g for 10 minutes at 24° C. In a typical experiment, PRP is preincubated for 5 minutes at 37° C, a compound of the invention is then added and the mixture incubated for one minute. After the addition of prostaglandin $E_1$ ($PGE_1$) and an additional 40 seconds of mixing, adenosine diphosphate (ADP) (20 μM) is added and the optical transmission recorded for three minutes. The rate of change, or initial velocity, of the optical transmission is measured by determining the slope of the steepest part of the curve in mm/minute.

Following the phosphodiesterase procedure described in section B the previously listed compounds numbered from 1 to 12 show activity as inhibitors of cyclic AMP phosphodiesterase.

The following examples illustrate the present invention without, however, limiting the same thereto.

EXAMPLES 1 to 12

The foregoing procedure for aggregation of blood platelets is followed except that each of the compounds listed in Column I of the table set out below is added alone, and in addition to $PGE_1$. The percent inhibition of platelet aggregation of the compound used alone is given in Column II, the percent inhibition of the $PGE_1$ alone is given in Column III, and the percent inhibition of the compound used in conjunction with $PGE_1$ is given in Column IV.

TABLE

| Column No. | I | | II | III | IV |
|---|---|---|---|---|---|
| | Compound (concentration) | Compound alone | $PGE_1$ alone | Compound + $PGE_1$ | |
| 1. | 2-[(Dimethylamino)methyl]-3,4-dihydro-7-methoxy-1(2H)-naphthaleneone, hydrochloride (1:1) | (100 μM) | −8 | 54 | 100 |
| 2. | 4-(Butylamino)-1-ethyl-1H-pyrazolo[3,4-b]pyridine-5-carboxylic acid, ethyl ester | (100 μM) | −18 | 51 | 76 |
| 3. | Hexamethylenebis(trimethylammonium-2-anthraquinonesulfonate) | (1000 μM) | −2 | 44 | 71 |
| 4. | 6,7-Diethoxy-1-(4,5-diethoxybenzyl)-isoquinoline hydrochloride | (100 μM) | −9 | 53 | 83 |
| 5. | 4-Chloro-1-ethyl-3-methyl-1H-pyrazolo[3,4-b]pyridine-5-acetonitrile | (200 μM) | −6 | 53 | 93 |
| 6. | 1-Ethyl-4-(isopropylidenehydrazino)-3-methyl-1H-pyrazolo[3,4-b]pyridine-5-carboxylic acid, ethyl ester, hydrochloride, hemihydrate | (1000 μM) | 0 | 41 | 78 |
| 7. | 2-Methyl-6-phenyl-4-(1-piperidinyl)-2H-pyrazolo[3,4-b]pyridine, hydrochloride (1:2) | (100 μM) | −24 | 51 | 65 |
| 8. | 3-Ethyl-7,12-dimethylpyrazolo[4',3':5,6]pyrido[4,3-b][1,5]benzodiazepin-6(3H)-one | (200 μM) | 13 | 53 | 84 |
| 9. | 3-Ethyl-7,12-dihydro-9-methoxy-7,12-dimethyl-pyrazolo[3',4':2,3]pyrido[4,5-b][1,5]benzodiazepin-6(3H)-one | (1000 μM) | 15 | 51 | 96 |
| 10. | 4-(Butylamino)-1H-pyrazolo[3,4-b]pyridine-6-carboxylic acid, ethyl ester | (100 μM) | −10 | 42 | 60 |
| 11. | 4-(Butylamino)-1-ethyl-1,7-dihydro-7-hydroxy-5H-furo[3,4-e]pyrazolo[3,4-b]pyridin-5-one | (1000 μM) | 1 | 47 | 91 |
| 12. | 10-Chloro-3-ethyl-7,12-dimethyl-7-12-dihydro-pyrazolo[4',3':5,6]pyrido[4,3-b][1,5]-benzodiazepin-6(3H)-one | (1000 μM) | 5 | 47 | 94 |

The results as shown in Columns II-IV of the Table clearly show that the activity of $PGE_1$ in inhibiting aggregation of blood platelets is clearly enhanced by employing $PGE_1$ in combination with compounds 1 to 12 (which also function as inhibitors of cyclic AMP phosphodiesterase (PDE)).

What is claimed is:

1. A method of inhibiting aggregation of human blood platelets which comprises contacting the platelets with $PGE_1$ and a compound which potentiates the effectiveness of $PGE_1$, which compound is a member selected from the group consisting of
   4-(Butylamino)-1-ethyl-1H-pyrazolo[3,4-b]pyridine-5-carboxylic acid, ethyl ester
   4-Chloro-1-ethyl-3-methyl-1H-pyrazolo[3,4-b]pyridine-5-acetonitrile
   1-Ethyl-4-(isopropylidenehydrazino)-3-methyl-1H-pyrazolo[3,4-b]pyridine-5-carboxylic acid, ethyl ester, or its hydrochloride, hemihydrate
   3-Ethyl-7,12-dimethylpyrazolo[4',3':5,6]pyrido[4,3-b]-[1,5]benzodiazepin-6-(3H)-one
   3-Ethyl-7,12-dihydro-9-methoxy-7,12-dimethyl-pyrazolo[3',4':2,3]pyrido[4,5-b][1,5]benzodiazepin-6(3H)-one
   4-(Butylamino)-1H-pyrazolo[3,4-b]pyridine-6-carboxylic acid, ethyl ester
   4-(Butylamino)-1-ethyl-1,7-dihydro-7-hydroxy-5H-furo-[3,4-e]pyrazolo[3,4-b]pyridin-5-one
   10-Chloro-3-ethyl-7,12-dimethyl-7,12-dihydropyrazolo-[4',3':5,6]pyrido[4,3-b][1,5]benzodiazepin-6(3H)-one, said $PGE_1$ being present in a concentration of from about $10^{-6}$ molar to about $10^{-9}$ molar, and said compound being present in a concentration of from about 0.1 mM to about 4 mM.

2. A method according to claim 1 wherein the human blood platelets are in whole human blood.

3. A method according to claim 1 wherein the human blood platelets are in platelet rich plasma.

4. A method according to claim 1 wherein the human blood platelets are in platelet concentrate.

5. A composition for inhibiting aggregation of human blood platelets which comprises $PGE_1$ and a member which potentiates the effectiveness of $PGE_1$, which member is selected from the group consisting of
   4-(Butylamino)-1-ethyl-1H-pyrazolo[3,4-b]pyridine-5-carboxylic acid, ethyl ester
   4-Chloro-1-ethyl-3-methyl-1H-pyrazolo[3,4-b]pyridine-5-acetonitrile
   1-Ethyl-4-(isopropylidenehydrazino)-3-methyl-1H-pyrazolo[3,4-b]pyridine-5-carboxylic acid, ester, or its hydrochloride, hemihydrate
   3-Ethyl-7,12-dimethylpyrazolo[4',3':5,6]pyrido[4,3-b]-[1,5]benzodiazepin-6-(3H)-one
   3-Ethyl-7,12-dihydro-9-methoxy-7,12-dimethyl-pyrazolo[3',4':2,3]pyrido [4,5-b][1,5]benzodiazepin-6(3H)-one
   4-(Butylamino)-1H-pyrazolo[3,4-b]pyridine-6-carboxylic acid, ethyl ester
   4-(Butylamino)-1-ethyl-1,7-dihydro-7-hydroxy-5H-furo[3,4-e]pyrazolo[3,4-b]pyridin-5-one
   10-Chloro-3-ethyl-7,12-dimethyl-7,12-dihydropyrazolo-[4',3':5,6]pyrido[4,3-b][1,5]benzodiazepin-6(3H)-one, said $PGE_1$ being present in a concentration of from about $10^{-6}$ molar to about $10^{-9}$ molar, and said member being present in a concentration of from about 0.1 mM to about 4 mM 6. The method as defined in claim 1 wherein said compound is
3-ethyl-7,12-dihydro-9-methoxy-7,12-dimethyl-pyrazolo-[3',4':2,3]pyrido[4,5-b][1,5]benzodiazepin-6(3H)-one.

7. The composition as defined in claim 6 wherein said member is
3-ethyl-7,12-dihydro-9-methoxy-7,12-dimethyl-pyrazolo-[3',4':2,3]pyrido[4,5-b][1,5]benzodiazepin-6-(3H)-one.

* * * * *

UNITED STATES PATENT OFFICE
CERTIFICATE OF CORRECTION

Patent No. 4,051,236                    Dated September 27, 1977

Inventor(s) Don Navarro Harris et al

It is certified that error appears in the above-identified patent and that said Letters Patent are hereby corrected as shown below:

Column 1, line 36, "plateletrich" should read --platelet-rich--.
Columns 5 and 6, in the Table, the column headings should be positioned as follows:

--

| Column No. | I<br>Compound | (concen-<br>tration) | % Inhibition of<br>Platelet Aggregation | | |
|---|---|---|---|---|---|
| | | | II<br>Compound<br>alone | III<br>$PGE_1$<br>alone | IV<br>Compound<br>+ $PGE_1$ |
| 1. 2-[(Dimethylamino)methyl]-3,4-dihydro-7-methoxy-1(2$\underline{H}$)-naphthaleneone, hydrochloride (1:1) | | (100 µM) | -8 | 54 | 100 |

--.

Column 6, line 52, before "ester" insert --ethyl--.
Column 6, line 68, after "4mM" insert a period.
Column 8, line 1, "claim 6" should read --claim 5--.

Signed and Sealed this

Seventh Day of February 1978

[SEAL]

Attest:

RUTH C. MASON
Attesting Officer

LUTRELLE F. PARKER
Acting Commissioner of Patents and Trademarks